United States Patent [19]

Hammar et al.

[11] 3,969,505

[45] July 13, 1976

[54] 8-N-METHYLPIPERAZINYL-N'-CARBONYLDIBENZOBICYCLOOCTADIENE AND SALTS THEREOF

[75] Inventors: Walton James Hammar, St. Paul; Alvin C. Conway, North St. Paul, both of Minn.

[73] Assignee: Riker Laboratories, Inc., Northridge, Calif.

[22] Filed: July 11, 1975

[21] Appl. No.: 595,288

Related U.S. Application Data

[62] Division of Ser. No. 339,359, March 8, 1973, Pat. No. 3,904,630.

[52] U.S. Cl. .............................................. 424/250
[51] Int. Cl.² ....................................... A61K 31/495
[58] Field of Search ................................... 424/250

*Primary Examiner*—Stanley J. Friedman
*Attorney, Agent, or Firm*—Alexander, Sell, Steldt & DeLaHunt

[57] ABSTRACT

The novel compound 8-N-methylpiperazinyl-N'-carbonyldibenzobicyclo[3.2.1]octadiene and its pharmaceutically acceptable acid addition salts are useful as sedatives and tranquilizing agents.

1 Claim, No Drawings

8-N-METHYLPIPERAZINYL-N'-CARBONYL-DIBENZOBICYCLOOCTADIENE AND SALTS THEREOF

This is a division of application Ser. No. 339,359 filed Mar. 8, 1973, now U.S. Pat. No. 3,904,630.

BACKGROUND OF THE INVENTION

1. Field of the Invention

This invention relates to the compound 8-N-methylpiperazinyl-N'-carbonyldibenzobicyclo[3.2.1]octadiene and its pharmaceutically acceptable salts. The invention also relates to processes for synthesizing, processes for using, and pharmaceutical compositions containing the compounds of the invention.

2. Prior Art

Compounds wherein the dibenzobicyclo[3.2.1]octadiene nucleus is bonded at the 8 position through carbonyl or alkylene groups to an amino group are known. German Offenlegungsschrift No. 1,953,334 describes numerous derivatives of 5-hydroxydibenzobicyclo[3.2.1]octadiene and three derivatives of the dibenzobicyclo[3.2.1]octadiene nucleus, including 8-carboxamidodibenzobicyclo[3.2.1]octadiene and 8-aminomethyldibenzobicyclo[3.2.1]octadiene. It should be noted that these compounds can also be named as 5,10-methano-5H-dibenzo[a,d]cycloheptene derivatives, and are sometimes thus described in the prior art. These compounds are described as diuretics.

German Offenlegungsschrift No. 2,216,884, a reference published subsequent to the present invention, describes antidepressant and anticonvulsant components wherein an amino residue ($-NR_1R_2$) is linked to a dibenzobicyclo[3.2.1]octadiene nucleus at the 8 position, i.e. an alkylene or alkenylene group.

Neither of these references of the prior art discloses or suggests the use of compounds containing the dibenzobicyclooctadiene nucleus as sedatives and tranquilizers, which is the utility of the compounds of the present invention.

So far as is known, the prior art has not provided N-methylpiperazinylamide derivatives and has not described or suggested the unique and unexpected activity of the compounds of the present invention.

The prior art references further do not disclose or suggest the significance of the geometrical isomerism of compounds of the 8-substituted dibenzobicyclo[3.2.1]octadiene type. It has been found that the anti-isomeric compounds of the present invention have a significantly improved therapeutic ratio when compared to the corresponding syn-isomer; and for the uses contemplated herein, the compounds having the anti configuration are preferred.

DETAILED DESCRIPTION OF THE INVENTION

The invention relates to compounds having the formula which is

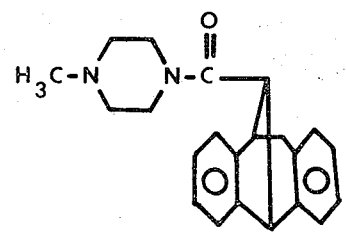

named herein (in anti configuration) as 8-anti(N-methylpiperazinyl-N'-carbonyl)dibenzobicyclo[3.2.1]octadiene, and its pharmaceutically acceptable salts. This invention also relates to processes for synthesizing, processes for using, and compositions containing the compounds of the invention.

Compounds of the invention are prepared in the free base form by the reaction of N-methylpiperazine with an acyl halide derivative, preferably the chloride, of 8-syn or 8-anti-carboxydibenzobicyclo[3.2.1]octadiene, in solution in an inert solvent such as dichloromethane, chloroform, benzene, hexane and the like. The reaction proceeds rapidly to completion in less than one hour at 20° to 30° C. The product is readily isolated by removal of the solvent, and is purified by recrystallization or other conventional methods.

The necessary intermediates, 8-syn and 8-anti-carboxydibenzobicyclo[3.2.1]octadiene are prepared from the known compound 8-anti-chlorodibenzocyclo[3.2.1]octadiene, see J. Am. Chem. Soc. 87, 2877 (1965). The chloro compound is converted by a Grignard reaction to the magnesium Grignard reagent, then reacted with carbon dioxide to prepare the corresponding 8-syn and 8-anti-carboxylic acids.

The carboxylic acid is converted to the corresponding acyl halide by reaction with an inorganic acid halide. It has been found that thionyl chloride reacts readily with 8-syn or 8-anti-carboxydibenzobicyclo[3.2.1]octadiene when the reactants are mixed and briefly heated at their reflux temperature (up to one hour). The acid chloride can be recovered by evaporating excess thionyl chloride and used as described hereinabove without further purification.

The free base product is readily converted to an acid addition salt by treatment with an approximately equimolar quantity of an acid. This has routinely been accomplished by treating the free base in isopropyl alcohol with acid to precipitate the product salt. Optionally, the precipitation may be facilitated by the addition of a non-solvent. Suitable pharmaceutically acceptable acid addition salts of the invention may be organic or inorganic and include the hydrochloride, hydrobromide, maleate, sulfate, phosphate, acetate, lactate, tartrate, citrate, organic sulfonates such as methanesulfonates, and the like.

The compounds of the invention have been found to be active in standard pharmacological screening tests to detect tranquilizing activity in mammals. The compound has been found to antagonize aggregation-induced mortality following the administration of amphetamine, a test described by Lasagna, L. and McCann, W. P., Science 125:1241 (1957); Burn, J. H. and Hobbs, R., Arch. int. Pharmacodyn 113:290 (1958), and others.

In this test, male mice (17–27 g.), ten mice per cage, are administered the test compound and returned to a stock cage for 30 minutes prior to a 10 mg./kg. i. p. injection of d,l-amphetamine sulfate. Immediately after amphetamine administration, the group of ten mice is placed in a rectangular glass jar approximately 6×5×10. A vehicle-pretreated (control) group is similarly included in another jar. The aggregation of animals within about a 30 square inch area produces mortality following the amphetamine dose which is non-lethal in individually caged mice. Over a five hour period of aggregation, positive control mice exhibit greater than 70 percent mortality, usually 90–100 percent. Positive control mice are vehicle-pretreated and amphetamine challenged. Active compounds protect against the incidence of group mortality, often reducing the five hour mortality to zero at effective doses.

The compounds also demonstrate tranquilizing activity in mammals by their ability to inhibit spontaneous locomotor activity. In this test, single male mice (16–24 g.) are weighed and administered the test compound at suitable geometrically spaced doses. Immediately following the dose, each treatment group, consisting of 15 mice each, is placed within the counting chamber of Woodard activity cages. The cumulative activity counts, resulting from mice interrupting infrared light beams within the counting chamber, are noted 15, 30, 45, 60 and 90 minutes after entry. The ratio of the mean tally of three cages per treatment to the mean tally of three control (vehicle only) treated mice is determined and a value of less than unity evaluated as a depressant effect. Additional tests which have been used and which demonstrate tranquilizing activity in the compound of the invention include the Sidman avoidance assay in rats and the antagonism of caffeine-induced locomotor stimulation in mice.

The compounds of the invention may be administered by the intraperitoneal or oral route. When administered intraperitoneally, they are administered in solution in a pharmaceutically acceptable solvent, in doses of about 1 to 30 milligrams per kilogram of body weight of the subject. It is presently preferred to use doses of from 2 to 20 milligrams per kilogram of the anti-isomer, since doses in this range have been found to be quite effective in animal tests. Such doses provide good therapeutic ratios, because the intraperitoneal $LD_{50}$ has been measured to be approximately 282 mg./kg. for the hydrochloride salt.

Administering the hydrochloride salt orally, doses of 10 to 50 mg./kg. are used to provide a tranquilizing effect. As the oral $LD_{50}$ is greater than 800 mg./kg., therapeutic ratios of 40 and greater are found for the preferred anti-isomer.

When a subject is treated with the compound of the invention, the dose must be varied according to the response of the subject and the age, weight, general health and the like. Control of this variation is within the skill of the medical practitioner.

The compound of the invention and its salts are administered in any of the conventional drug dosage forms. The salts are readily water-soluble, and solutions in the known pharmaceutical extending media, or pills or capsules, can be prepared and employed as desired. Both the compound and its salts are solids and are readily combined with diluents to provide pharmaceutical dosage forms of various types.

The compound and its salts generally have been found to incorporate some water of crystallization.

The following examples are provided to illustrate the best mode presently known for the preparation of the compound of the invention, and its salts, and are not intended to be limiting of the invention described hereinabove.

EXAMPLE 1

To a suspension of 3.15 g. (0.130 mole) of magnesium filings in 20 ml. of tetrahydrofuran are added 29.5 g. (0.126 mole) of 8-anti-chlorodibenzobicyclo[3.2.-1]octadiene while maintaining the solution at reflux. Five drops of 1,2-dibromomethane are added. The mixture is maintained at reflux temperature for about 16 hours. The mixture is then cooled to −25° C. with a Dry Ice-acetone bath, and carbon dioxide is bubbled in rapidly. The addition of carbon dioxide is continued for 1.5 hours, then the mixture is warmed to room temperature. The mixture is then added carefully to an aqueous solution saturated with ammonium chloride. The water layer is separated and extracted with dichloromethane, then extracted twice with diethyl ether, and the organic layers are combined. The combined organic layers are evaporated under reduced pressure to a non-volatile residue. Diethyl ether is added, and the ether solution is washed with an equal volume of 5 percent aqueous sodium hydroxide solution twice. The aqueous solution is then acidified, washed with dichloromethane; the dichloromethane extracts are combined and dried over magnesium sulfate. This solution is filtered, and the filtrate is evaporated under reduced pressure to provide 8-carboxydibenzobicyclo[3.2.-1]octadiene. This solid product is fractionally recrystallized from benzene to provide a white solid, melting point 175°–180° C. Nuclear magnetic resonance analysis of this isomer shows it to be essentially pure (greater than 95 percent) anti-isomer.

| Analysis: | | %C | %H |
|---|---|---|---|
| | Calculated for $C_{17}H_{14}O_2$: | 81.5 | 5.64 |
| | Found: | 81.8 | 5.60 |

The mother liquors from the recrystallization of the anti-isomer are evaporated to provide a residue which is fractionally recrystallized from benzene or ethanol. The essentially pure syn dl isomer is obtained which has m.p. 218°–222° C. Its purity is checked by its nuclear magnetic resonance spectrum.

It should be noted that the amount of syn-isomer obtained is substantially descreased by maintaining the temperature of the solution to which carbon dioxide is added at −55° C. until the aqueous ammonium chloride solution is added.

EXAMPLE 2

A solution of 50 ml. of thionyl chloride and 7.8 g. (0.032 mole) of anti-8-carboxydibenzobicyclo[3.2.-1]octadiene is heated to its reflux temperature and maintained at that temperature for one hour. The excess thionyl chloride is removed by evaporation under reduced pressure. Benzene is added (about 50 ml.), and the mixture is again evaporated to dryness under reduced pressure. The solid product is anti-8-carboxydibenzobicyclo[3.2.1]octadiene chloride, m.p. 102°–104° C.

EXAMPLE 3

The anti-8-carboxydibenzobicyclooctadiene chloride product (0.032 mole) from Example 2 is dissolved in dichloromethane, and N-methylpiperazine (10 g., 0.10 mole) is added with stirring. After 30 minutes the mixture is washed successively with equal volumes of water, saturated sodium bicarbonate solution and saturated sodium chloride solution. The organic layer is then dried over anhydrous sodium sulfate and filtered; then the filtrate is evaporated under vacuum, giving an oil which solidifies when washed with hexane. The solid product is triturated with hexane and filtered, yielding the solid free base, 8-anti-(N-methylpiperazino-N'-carbonyl)dibenzobicyclo[3.2.1]octadiene, m.p. 172°–174° C. (uncorrected). The structural assignment is supported by its infrared spectrum.

EXAMPLE 4

To a suspension of 8-anti-(N-methylpiperazino-N'-carbonyl)dibenzobicyclo[3.2.1]octadiene base (8.5 g., 0.039 mole) in 100 ml. of isopropanol are added 7 ml. of 7M hydrogen chloride in isopropanol, forming the hydrochloride salt. The solution is then treated with diisopropyl ether to cause precipitation of the salt, which is separated by filtration. The solid is recrystallized from a mixture of isopropyl alcohol and diisopropyl ether. A tan solid, 8-anti-(N-methylpiperazino-N'-carbonyl)dibenzobicyclo[3.2.1]octadiene hydrochloride is obtained, m.p. 265°–267° C.

| Analysis: | %C | %H | %N |
|---|---|---|---|
| Calculated for $C_{22}H_{24}N_2O \cdot HCl \cdot \tfrac{1}{2} H_2O$: | 69.4 | 6.8 | 7.4 |
| Found: | 69.9 | 6.9 | 7.4 |

EXAMPLE 5

Using the methods described in Examples 2, 3 and 4, 8-syn-carboxydibenzobicyclo[3.2.1]octadiene is converted to white solid 8-syn-(N-methylpiperazine-N'-carbonyl)dibenzobicyclo[3.2.1]octadiene hydrochloride, m.p. 265°–267° C.

| Analysis: | %C | %H | %N |
|---|---|---|---|
| Calculated for $C_{22}H_{24}N_2O \cdot HCl \cdot \tfrac{1}{4} H_2O$: | 70.8 | 6.9 | 7.5 |
| Found: | 70.9 | 6.9 | 7.3 |

What is claimed is:

1. The method for effecting sedative action upon the mammalian central nervous system which comprises administering an effective amount of a compound of the group consisting of 8-anti-(N-methylpiperazinyl-N'-carbonyl)dibenzobicyclo[3.2.1]octadiene and a pharmaceutically acceptable salt thereof to a mammalian subject.

* * * * *